United States Patent [19]

Rasco et al.

[11] Patent Number: 4,828,846

[45] Date of Patent: May 9, 1989

[54] HUMAN FOOD PRODUCT PRODUCED FROM DRIED DISTILLERS' SPENT CEREAL GRAINS AND SOLUBLES

[75] Inventors: Barbara A. Rasco, Seattle; William J. McBurney, Edmonds, both of Wash.

[73] Assignee: Washington Research Foundation, Seattle, Wash.

[21] Appl. No.: 144,624

[22] Filed: Jan. 11, 1988

Related U.S. Application Data

[63] Continuation of Ser. No. 799,010, Nov. 18, 1985, abandoned.

[51] Int. Cl.[4] .......................... A23J 1/12; A23L 1/105
[52] U.S. Cl. ......................................... 426/18; 426/20; 426/21; 426/27; 426/28; 426/31; 426/618; 426/640; 426/653; 426/656; 426/44; 426/52; 426/648
[58] Field of Search ....................... 426/44, 49, 52, 18, 426/27, 28, 31, 20, 21, 618, 640, 653, 656, 648

[56] References Cited

U.S. PATENT DOCUMENTS

3,249,512 5/1966 Bode ...................................... 426/18
3,958,015 5/1976 Gay ........................................ 426/44

OTHER PUBLICATIONS

G. N. Bookwalter et al., "Corn Distillers' Grains and Other By Products of Alcohol Production in Blended Foods, II. Sensory, Stability, and Processing Studies", *Cereal Chemistry*, 61(6)1984:509-513.
Letter of R. Kostak, dated Nov. 3, 1982 from Protein Alpha, Inc., Rupert, Idaho to ppa. Karr & Co., Inc.
M. M. Morad et al., "Utilization of Dried Distillers' Grain from Sorghum in Baked Food Systems", *Cereal Chemistry*, 61(5) 1984:409-414.
John W. Finley, Charles E. Walker and Earl Hautala, "Utilization of Press Water from Brewer's Spent Grain", *Science Food Agriculture*, 1976, 27, 655-660.
Satterlee et al., "The Chemical Functional and Nutritional Characterization of Protein Concentrates from Distiller's Grains", *Cereal Chemistry*, 53(5): 739-749.
J. S. Wall et al. "Corn Distillers", Grains and Other By-Products of Alcohol Production in Blended Foods, I. Compositional and Nutritional Studies, *Cereal Chemistry*, 61(6)1984, 504-509.
N. Prentice, L. T. Kissell, R. C. Lindsay and W. T. Yamazaki, "High-Fiber Cookies Containing Brewers' Spent Grain", *Cereal Chemistry*, 55(5)1978, 712-721.
N. Prentice, "Brewers' Spent Grain in High Fiber Muffins", *The Bakers Digest*, Oct. 1978, p. 22.
J. W. Finley and M. M. Hanamoto, "Milling and Baking Properties of Dried Brewer's Spent Grains", *Cereal Chemistry*, 57(3)1980:166-168.
Cho C. Tsen et al., "Evaluation on the Quality of Cookies Supplemented with Distillers' Dried Grain Flours", *Journal of Food Science*, 47(2)1982:684-685.
Irene E. Eidet et al., "Making Quick Breads with Barley Distillers' Dried Grain Flour", *The Bakers Digest*, Sep. 11, 1984.
P. C. Dreese et al., "Baking Properties of the Bran Fraction from Brewer's Spent Grains", *Cereal Chemistry*, 59(2)1982:89-91.
Y. Pomeranz et al., "White Wheat Bran and Brewer's Spent Grains in High-Fiber Bread", *The Bakers Digest*, Dec. 1976, pp. 35-38.
T. Kissell et al., "Protein and Fiber Enrichment of Cookie Flour with Brewer's Spent Grain", *Cereal Chemistry*, 56(4)1979:261-266.
N. Prentice and B. L. D'appolonia, "High-Fiber Bread Containing Brewer's Spent Grain", *Cereal Chemistry*, 54(5)1977:1084-1095.
David Hudson, "Making Biscuits and Bread from Spent Grain", *Brewing and Distilling International*, Sep. 1984, pp. 42-43.
Kari R. Dawson et al., "Taste Panel Preference Correlated with Lipid Composition of Barley Dried Distillers' Grains", *Journal of Food Science*, vol. 49(1984):787-790.
Daniel J. Wampler et al., "Utilization of Distillers' Spent Grain in Extrusion Processed Doughs", *Journal of Food Science*, 49(1984):1321-1322.
Y. V. Wu, K. R. Sexson and J. S. Wall, "Protein-Rich Residue from Corn Alcohol Distillation: Fractionation and Characterization", *Cereal CHemistry*, 58(4)1981:343-347.

(List continued on next page.)

*Primary Examiner*—Marianne Cintins
*Attorney, Agent, or Firm*—Seed and Berry

[57] ABSTRACT

A food product suitable for human consumption, having acceptable flavor and nutritional value, is recovered from cereal grain residues remaining after alcohol fermentation. The food product of the invention is produced by controlling the pH at a range of 4.0-5.0 of the various enzymic conversions of starch to alcohol using only certain organic and inorganic acids which avoid imparting unacceptable mineral acid tastes to the finished product. The preferred acid is citric acid. The pH of the slurry residues before drying to a finished product must be neutralized to about 5.0-8.0. Again, satisfactory taste of the finished product is achieved by carefully selecting the neutralizing agent, typically hydroxides or oxides of Na, K or Ca. Resulting products are characterized as containing only salts from acids used to adjust pH which are taste acceptable. The product forms a 1:10 aqueous suspension having a pH of about 5.0-8.0. In addition, the products include ions from the neutralizing agents, typically three times higher in concentration than concentrations for the same ions in the grain feedstock. The neutralizing ions are individually selected and are of such a concentration which produces food products that are acceptable in taste and are not toxic to humans.

24 Claims, No Drawings

OTHER PUBLICATIONS

Joseph S. Wall et al., "Effect of Recycling Distillers' Solubles on Alcohol and Feed Production from Corn Fermentation", *Journal of Agriculture Food Chemistry*, 31(4)1983:770–775.

G. S. Ranhotra et al., "Nutritional Characteristics of Distiller's Spent Grain", *Journal of Food Science*, 47(1982):1184–1186.

Y. Victor et al., "Corn Distillers' Dried Grains with Solubles and Corn Distillers' Dried Grains: Dry Fractionation and Composition", *Journal of Food Science*, 47(4)1928:1155–1157 and 1180.

Y. V. Wu, K. R. Sexson and A. A. Lagoda, "Protein-Rich Residue from Wheat Alcohol Distillation: Fractionation and Characterization", *Cereal Chemistry*, 61(5)1984:423–427.

Y. V. Wu and K. R. Sexson, "Fractionation and Characterization of Protein-Rich Material from Sorghum Alcohol Distillation", *Cereal Chemistry*, 61(5)1984:388–391.

Y. V. Wu, "Fraction and Characterization of Protein-Rich Material from Barley After Alcohol Distillation", *Cereal Chemistry* (Draft), May 22, 1985:1–19.

HUMAN FOOD PRODUCT PRODUCED FROM DRIED DISTILLERS' SPENT CEREAL GRAINS AND SOLUBLES

This application is a continuation of U.S. patent application Ser. No. 799,010, filed Nov. 18, 1985, now abandoned.

TECHNICAL FIELD

The products and process of the invention relate to recovering the food value of residues from starch-containing cereals and the like remaining after fermentation of the cereals for production of the ethanol. More particularly, the invention focuses on producing a dried residue from the alcohol recovery process that is suitable for human food use.

BACKGROUND OF THE INVENTION

Production of ethanol from agricultural products using yeast is one of the most important and best-known industrial fermentations. This fermentation is of immense importance to brewers and distillers, bakers and chemical manufacturers. Several processes for the manufacture of fuel-grade ethanol from molasses, corn, grain sorghum and wheat are well known.

Corn is the most popular grain used commercially to manufacture fuel alcohol. The process typically involves a two-stage enzymic conversion of starch to sugar, followed by fermentation and then a distillation to recover alcohol and carbon dioxide. Manufacturers typically dry the grain residue and sell the dried product, commonly called "distillers' dried grains," as an animal feed or a component of other animal feed products. The solubles portion of the residue is often dried separately. Many smaller manufacturers dewater the distillers' grains and ship them in wet form to local feed lots or dairy farms. In these situations, the soluble component of the distillers' grains is generally discarded.

At the present time wheat is not an economical choice as a fermentation substrate unless the spent grains and solubles can be sold for a higher price as human food rather than animal feed. Wheat residues are generally higher in protein, lysine, and threonine than corn residues. The process for manufacturing ethanol from wheat is very similar to that of corn.

Utilization of fermentation residues has received little attention beyond use in animal feeds. A major problem with distillers' grain residue is that it possesses a distinct odor and taste which negatively affect acceptability even for use in animal feed. Bookwalter et al., in "Investigation on the Use of Distillers' Grains or Fractions Thereof in Blended Foods for the Foods for Peace Program and Other Food Applications," USDA Agricultural Research Service (1983), report using solvent extraction and neutral water rinses in an attempt to remove oxidized lipid and fermentation by-products to produce a better tasting product. These attempts were unsuccessful. Tsen et al., in "Evaluation of the Quality of Cookies Supplemented With Distillers' Dried Grain Flour," *J. Food Science* 47(2) 684 (1982), report that the protein quality and nutritive value of the grain residues deteriorates with harsh heat treatments. Others have noted that nutritional value and overall acceptability vary widely among commercial samples, depending upon how they were processed. Prentice et al., in "High Fiber Bread Containing Brewer's Spent Grains," *Cereal Chem.* 54:1084 (1977), and "High Fiber Cookies Containing Brewer's Spent Grains," *Cereal Chem.* 55:712 (1978), report experiments using dried brewers' grains as a baking ingredient for human food. In general, the experiments were not successful. Tsen et al. report that product volume, color, and overall acceptability for bread, sugar, spice cookies and brownies produced were significantly less than for similar products containing no distillers' grain residue, even where substitution levels were 15% or less. Only chocolate chip cookies containing 15% dried distillers' grain residues were as acceptable as chocolate chip cookies containing no distillers' grains.

DISCLOSURE OF INVENTION

It is an object of the invention to produce a food product suitable for human consumption from residues remaining after conversion of a starch-containing cereal grain to alcohol by fermentation. The food product of the invention is achieved by selecting and using acids and bases for adjusting the pH of the grain suspension during processing such that the resulting products are organoleptically and toxicologically acceptable. A preferred process includes conversion of starch to sugars, fermentation with yeast to produce alcohol, removing the alcohol from the residues, and dehydrating the residues. The resulting product has improved taste acceptability while retaining nutritional value.

In the process of the invention, the starch-containing cereal grains are suspended in water and partially hydrolyzed and liquified with a first enzyme to convert the starch content of the grains into dextrins. The pH of the slurry suspension is then adjusted to 4.0-5.0 using an organoleptically acceptable acid, preferably only organic acids or certain inorganic acids. The slurry is saccharified with a second enzyme to complete conversion of the starch into glucose. The sugar is fermented using yeast to convert substantially all the sugar to alcohol. The alcohol is then removed from the slurry. The remaining slurry residues are neutralized by adjusting the slurry pH to about 5.0-8.0 using certain acceptable alkali hydroxides or other basic oxides. The slurry residues are dried to a moisture content of 5-10% by weight in a manner which preserves the protein quality, nutritional value and light color of the product. Care is taken to ensure that the temperature of the product, during drying, does not exceed about 170° F.

A key element of the invention is adjusting the pH of the hydrolyzed slurry using an organic acid or certain inorganic acids which are selected to produce a product having an acceptable taste. The organic acid may be citric, malic, acetic, lactic, tartaric, fumaric or succinic acid, for example. The preferred inorganic acids are nitric and hydrochloric acids. The intent of using certain organic or inorganic acids is to avoid the use of conventionally used mineral acids, such as $H_2SO_4$, which impart an unacceptable taste to the finished products. The organic acids are preferred because they are akin to those acids produced as by-products during yeast fermentation. The preferred organic acid is citric acid.

A second key element is the utilization of only Ca, Na, K hydroxides or oxides, preferably, or other hydroxides or oxides alone or in combination, for neutralization before drying. The choice of and concentration of the agents used for pH adjustment are such that an organoleptically and toxicologically acceptable finished product is produced. Preferred finished products are produced by neutralizing to a pH of 5.0-8.0 using Ca, Na or K hydroxides or oxides wherein the resulting product has a total metal ion content of about three times that of the initial grain feedstock metal ion content. A preferred product includes Na, K and Ca in a concentration ratio of about 1:1:4, respectively.

BEST MODE FOR CARRYING OUT THE INVENTION

The invention is an improvement over the well-known processes for fermentation of grains that have a substantial starch content into alcohol. The best known process involves a two-stage enzymic conversion of starch to sugar, followed by fermentation and distillation for recovery of alcohol. Heretofore, the remaining grain residues were then dried to produce a product suitable for animal consumption. The improved process produces unique products that are suitable for human consumption.

In a preferred process of the invention, the starch-containing cereal grain, either as whole grains at approximately 40 mesh, or flour, is suspended in water to produce a 25-33% suspension or slurry. The slurry is adjusted to a pH of 6.0-6.5; and 50-80 ppm calcium, as calcium oxide or calcium chloride, is added. A thermally stable alpha-amylase is introduced into the slurry, at about 0.05% by weight on a dry starch basis, having a specific activity of about 170,000 MWU/g. "MWU" (Modified Wohlgemuth Unit) is defined as the activity required to hydrolyze one milligram of soluble starch to dextrins of a defined size within thirty minutes under specified assay conditions.

The reaction mixture is heated until the slurry tests "starch negative," and possesses a dextrose equivalent of 10-14. The slurry volume is then adjusted to about 18% solids. The temperature of the slurry is adjusted to about 135° F.

The pH of the slurry is carefully adjusted to 4.0-5.0 with an acceptable inorganic or organic acid. Acceptable organic acids include citric acid, malic acid, acetic acid, lactic acid, tartaric acid, fumaric acid or succinic acid, or mixtures thereof. The selection of the acid is a critical element of the invention, having a direct impact on the flavor of the ultimate product. The preferred acid is citric acid. A total concentration of 0.17 millimoles of anhydrous organic acid anion per 100 grams of dry product is preferred. Also acceptable are certain inorganic acids which do not adversely affect taste. To be avoided is the "bitter" or "metallic" taste imparted by the conventionally used sulfuric acid. Acceptable inorganic acids are nitric and hydrochloric acids.

A second enzymic reaction is conducted to complete conversion of the starch to glucose. Typically, a second enzyme is used to accomplish and complete the starch conversion. For example, amyloglucosidase, Diazyme ™ manufactured by Miles Laboratories, at a level of 10,000 Diazyme units per 100 lbs on a dry starch basis, requires a reaction time of 3-18 hours to convert the desired amount of starch to glucose.

Following saccharification, the slurry is fermented to convert the glucose to ethanol. The slurry is first cooled to 80°-85° F., and the pH is readjusted to 4.0-4.5, if necessary. The slurry is next inoculated with a yeast, typically at 2-6 lbs per 1,000 gallons. The fermentation step is carried to completion, until less than 20 mg glucose/liter remains in the fermentation broth. Fermentation time averages 55-75 hours. It is important that substantially all sugar be converted to alcohol, otherwise the product will turn brown in color upon drying.

The alcohol is removed from the fermentation broth by distillation of the suspension. The remaining slurry residue is concentrated to 30-40% solids by weight. Alternatively, the solids may be removed prior to distillation by, for example, centrifugation.

The pH of the concentrated residue is adjusted to about 5.0-8.0 using a suitable oxide or hydroxide. Again, selection of the neutralization agents and their amounts for this pH adjustment is critical to the taste acceptability of the finished product. The bases used, in combination with salts remaining in the residues from the previously used acids, must be organoleptically acceptable. "Organoleptically acceptable" means that a panel of consumers would find that incorporation of the food product of the invention as a component of foods in which flours similar to those of the invention are typically used produces products as acceptable as those without the product of the invention. Taste, odor and color acceptance by humans is, of course, a somewhat subjective aspect of a product characterization. However, the pH limitations defined are widely accepted limits of taste acceptability. Unless the residue slurry has a pH greater than about 5.0, the product will be rejected as too "sour" or acidic. The product will be rejected as "soapy" or too alkaline unless the slurry has a pH of less than or equal to 8.0.

The neutralization agents are preferably hydroxides or oxides of Na, K or Ca. Other organoleptically acceptable ions, such as Al or $NH_4$ are suitable. Often, a combination of ions produces the best result. Too much sodium may result in a metallic taste. A mixture of Na, K and Ca hydroxides or oxides is preferred. The most preferred mixture proportions of Na, K and Ca for a neutralizing agent are a 1:1:4 ratio, respectively. A distinctive characteristic of the finished product is a metal ion concentration of the neutralizing agents that is at least a multiple of three higher than the concentration of ions in the initial grain feedstock.

The residues are dried to a moisture content of 5-10% by weight. Drying is an important step in the processing and must be carefully controlled to preserve flavor, and particularly, color. The residues remaining in the suspension after concentration must not be subjected to a drying temperature such that the product temperature exceeds about 170° F. The products will turn brown in color and not be generally acceptable if exposed to excessive temperature. Any dehydrating or drying apparatus which dries the product to less than about 10% moisture content without exceeding 170° F. product temperature limit is acceptable. Thus, vacuum or flash dryers, steam tube dryers, spray dryers or the like are all suitable.

The finished product is suitable for use in human foods, having an acceptable taste and nutritional value. In a test run, acceptable products are characterized by a metal ion concentration of $\geq 0.2$ g sodium, $\geq 1.5$ g potassium, or $\geq 0.13$ g calcium per 100 g of finished product on a dry weight basis.

The product and process of the invention are suitable for recovering product from any cereal grain having a significant starch content. For example, red wheat, white wheat, corn, milo, barley, rice, rye or sweet sorghum, or mixtures thereof, are suitable. The starting material may be in the form of whole grains or flour. Also acceptable are high starch fractions produced by wet or dry milling operations.

Many of the processing conditions described above are a matter of choice by those skilled in the art. The only critical processing steps of the invention involve selection of the pH adjusting or neutralizing materials. The drying step, of course, as noted above, must be controlled to preserve the sensory and nutritional properties of the residues.

The product of the invention is most advantageously utilized as a food high in protein and dietary fiber, particularly as a component of various baking flours and the like. For example, the dried product of the invention may comprise up to 35% of brownies, chocolate chip, chocolate, spice, and lemon molasses cookies; 30–50% of yeast breads; and 30% of quick breads, producing a highly acceptable product. Products containing up to 20% of the product of the invention as a component of flours are indistinguishable from those flours not containing the products of the invention. The product of the invention has been successfully substituted in breading mixes at 20–30% flour replacement and as a 10–20% flour substitute in pastas made with water, egg, whole wheat or spinach. The food products of the invention are utilized basically as any high-fiber and hence, relatively coarse flours, such as whole wheat flour, for example.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A process for recovering a food product organoleptically and nutritionally suitable for human consumption from starch-containing cereal grains consisting essentially of:
    suspending a starch-containing grain in water;
    converting substantially all starch to alcohol with enzymes, yeast and an acid or acids which are selected to produce an organoleptically acceptable product, thereby producing an acidified suspension;
    removing the alcohol from the acidified suspension, thereby producing a dealcoholized acidified suspension;
    adjusting the pH of the dealcoholized acidified suspension to about 5.0–8.0 by adding a base or bases which are selected to produce an organoleptically acceptable product, thereby producing a suspension; and
    drying the resulting suspension such that the temperature of the suspended grain does not exceed 170° F., thereby producing a dried product which contains a soluble component.

2. The process of claim 1 wherein the acid or acids added are organic acids.

3. The process of claim 1 wherein the acid or acids added are selected from the group consisting of citric, malic, acetic, lactic, tartaric, fumaric, succinic, nitric and hydrochloric acids, or a combination thereof.

4. The process of claim 1 wherein the base or bases added are selected from the group consisting of the oxides and hydroxides of sodium, potassium, calcium, aluminum and ammonia, or a combination thereof.

5. The process of claim 1 wherein the cereal grains used are selected from the group consisting of red wheat, white wheat, corn, milo, barley, rice, rye and sweet sorghum, or a combination thereof.

6. A process for recovering a food product suitable for human consumption from cereal grain residues containing component, consisting essentially of:
    suspending a starch-containing grain in water to form a suspension;
    liquifying the suspension with a first enzyme to partially convert the starch content of the grain to dextrins;
    adjusting the pH of the suspension to 4.0–5.0 by adding acids which are selected to produce an organoleptically acceptable product, thereby producing an acidified suspension;
    saccharifying the acidified suspension with a second enzyme to complete the conversion of substantially all starch to sugar;
    fermenting the suspension with yeast to convert substantially all of the sugar into alcohol;
    removing the alcohol from the suspension by distillation, thereby producing a dealcoholized suspension;
    adjusting the pH of the dealcoholized suspension to greater than about 5.0 by adding a base selected to produce an organoleptically acceptable product; and
    drying the resulting suspension to about a 5%–10% moisture content such that the temperature of the suspended grain does not exceed 170° F., producing a dried product which is organoleptically acceptable for human food use and which contains a soluble component from the cereal grain.

7. The process of claim 6 wherein the first enzyme is a thermostable alpha-amylase and the second enzyme is an amyloglucosidase.

8. The process of claim 6 wherein the acid or acids added are organic acids.

9. The process of claim 6 wherein the acid or acids added are selected from the group consisting of citric, malic, acetic, lactic, tartaric, fumaric, succinic, nitric and hydrochloric acids, or a combination thereof.

10. The process of claim 6 wherein the base or bases added are selected from the group consisting of the oxides and hydroxides of sodium, potassium, calcium, aluminum and ammonia, or a combination thereof.

11. The process of claim 6 wherein the cereal grains used are selected from the group consisting of red wheat, white wheat, corn, milo, barley, rice, rye and sweet sorghum, or a combination thereof.

12. A dried food product suitable for human consumption consisting essentially of a mixture of:
    cereal grains having substantially all starch removed;
    solubles from distiller's dried grains; and
    an organoleptically acceptable salt, wherein said salt consists of an anion and a cation produced from an organoleptically acceptable acid or acids and an organoleptically acceptable base or bases in a concentration exceeding approximately three times that found naturally in the grains.

13. The food product of claim 12 in which there is more than one organoleptically acceptable salt produced from an organoleptically acceptable acid or acids and an organoleptically acceptable base or bases in a concentration exceeding approximately three times that found naturally in the grain.

14. The food product of claim 12 wherein the salt contains an organic acid anion.

15. The food product of claim 12 wherein the anion of the salt is selected from the group consisting of salts of citric, malic, acetic, lactic, tartaric, fumaric, succinic, nitric and hydrochloric acids, or a combination thereof.

16. The food product of claim 12 wherein the cation of the salt is selected from the group consisting of salts of sodium, potassium, calcium, aluminum and, ammonium ions, or a combination thereof.

17. The food product of claim 12 wherein the salts are salts of sodium, potassium and calcium present in a ration of about 1:1:4, respectively.

18. The food product of claim 12 wherein the pH of a 1:10 aqueous suspension is 5.0–8.0.

19. The food product of claim 12 wherein the pH of a 1:10 aqueous suspension is 6.0–7.2.

20. The food product of claim 12 wherein the salt concentrations are the equivalent of or greater than 0.2 grams sodium, 1.5 grams potassium, or 0.13 grams calcium per 100 grams of dry product.

21. The food product of claim 12, having a moisture content greater than or equal to 5% moisture and a protein content greater than or equal to 16% of dry weight.

22. A dried food product suitable for human consumption consisting essentially of a mixture of:
cereal grains having substantially all starch removed;
solubles from distiller's dried grains;
an organoleptically acceptable salt produced from an organoleptically acceptable acid or acids and an organoleptically acceptable base or bases in a concentration exceeding approximately three times that found naturally in the grains; and 0.17 millimoles of an anhydrous organic acid per 100 grams dry weight of dried product.

23. In a process for recovering a food product for human consumption with a soluble component from spent cereal grains wherein the cereal grains are used for alcohol production by:
suspending a starch-containing grain in water to form a suspension;
converting substantially all starch to alcohol with enzymes, yeast and acid;
removing the alcohol from the suspension to produce a dealcoholized suspension; and
drying the dealcoholized suspension to form a dried food product;
the improvement consisting essentially of the use of an organoleptically acceptable acid or acids in the converting step and by the addition of a step prior to the drying step of adjusting the pH of the dealcoholized suspension to about 5.0 to 8.0 by adding a base or bases which are selected to produce an organoleptically acceptable product and creating a food product which contains a soluble component.

24. In a process for recovering a food product suitable for human consumption from cereal grain residues containing a soluble component by:
suspending a starch-containing grain in water to form a suspension;
liquifying the suspension with a first enzyme to partially convert the starch content of the grain to dextrins;
adjusting the pH of the suspension by adding acids to produce an acidified suspension;
saccharifying the acidified suspension with a second enzyme to complete the conversion of substantially all starch to sugar;
fermenting the suspension with yeast to convert substantially all of the sugar into alcohol;
removing the alcohol from the suspension by distillation, thereby producing a dealcoholized suspension; and
drying the resulting dealcoholized suspension;
the improvement consisting essentially of the use of an acid or acids which are selected to produce an organoleptically acceptable product, and the addition of a step before the drying step of adjusting the pH of the dealcoholized suspension to greater than about 5.0 by adding a base selected to produce an organoleptically acceptable product and which contains a soluble component form the original cereal grain.

* * * * *

UNITED STATES PATENT AND TRADEMARK OFFICE
CERTIFICATE OF CORRECTION

PATENT NO. : 4,828,846

DATED : May 9, 1989

INVENTOR(S) : Barbara A. Rasco; William J. McBurney

It is certified that error appears in the above-identified patent and that said Letters Patent is hereby corrected as shown below:

In claim 13, column 6, line 66, delete "grain" and substitute therefor --grains--.

In claim 17, column 7, line 12, delete "ration" and substitute therefor --ratio--.

In claim 24, column 8, line 41, delete "form" and substitute therefor --from--.

Signed and Sealed this

Thirteenth Day of March, 1990

Attest:

JEFFREY M. SAMUELS

Attesting Officer     Acting Commissioner of Patents and Trademarks